(12) United States Patent
Kuksenkov et al.

(10) Patent No.: US 7,978,742 B1
(45) Date of Patent: Jul. 12, 2011

(54) METHODS FOR OPERATING DIODE LASERS

(75) Inventors: Dmitri Vladislavovich Kuksenkov, Big Flats, NY (US); Shenping Li, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 12/730,482

(22) Filed: Mar. 24, 2010

(51) Int. Cl.
*H01S 3/00* (2006.01)
(52) U.S. Cl. ................................. 372/38.02; 372/38.07
(58) Field of Classification Search .................... 372/11, 372/29.015, 38.02, 38.07
See application file for complete search history.

(56) References Cited

U.S. PATENT DOCUMENTS

| | | | | |
|---|---|---|---|---|
| 5,388,114 | A | 2/1995 | Zarrabi et al. | 372/22 |
| 5,418,802 | A | 5/1995 | Chwalck | 372/20 |
| 6,393,038 | B1 | 5/2002 | Raymond et al. | 372/22 |
| 6,650,673 | B2 | 11/2003 | Hong et al. | 372/50 |
| 6,879,606 | B1 | 4/2005 | Miesak | 372/31 |
| 7,173,950 | B2 | 2/2007 | Hand et al. | 372/22 |
| 2008/0175284 | A1 | 7/2008 | Konttinen et al. | 372/22 |

FOREIGN PATENT DOCUMENTS

| | | |
|---|---|---|
| WO | 95/25369 | 9/1995 |
| WO | 2008/087253 | 7/2008 |

OTHER PUBLICATIONS

"Visible laser sources based on frequency doubling in nonlinear waveguides"; Webjorn et al; IEEE Journal of Quantum Electronics, vol. 33, No. 10, Oct. 1997.

*Primary Examiner* — Armando Rodriguez
(74) *Attorney, Agent, or Firm* — Gregory V. Bean

(57) ABSTRACT

Methods for operating diode lasers are provided. According to one method, the diode laser comprises a wavelength selection section, a gain section and a saturable absorber. The method comprises applying a hybrid-control signal comprising a hybrid-control DC bias to the saturable absorber, and applying a hybrid-driving signal comprising a hybrid-driving DC bias and a hybrid-driving AC bias to the gain section. The hybrid signals are selected and the diode laser is configured such that a relatively high hybrid-control DC bias corresponds to a relatively low average of the output power of the diode laser, and a relatively low hybrid-control DC bias corresponds to a relatively high average of the output power of the diode laser. The hybrid-driving DC bias is between a switch-on threshold of the diode laser and a switch-off threshold of the diode laser, and the hybrid-driving AC bias is periodic. The hybrid-driving AC bias has a peak-to-peak amplitude greater than the difference between the switch-on threshold and the switch-off threshold.

20 Claims, 5 Drawing Sheets

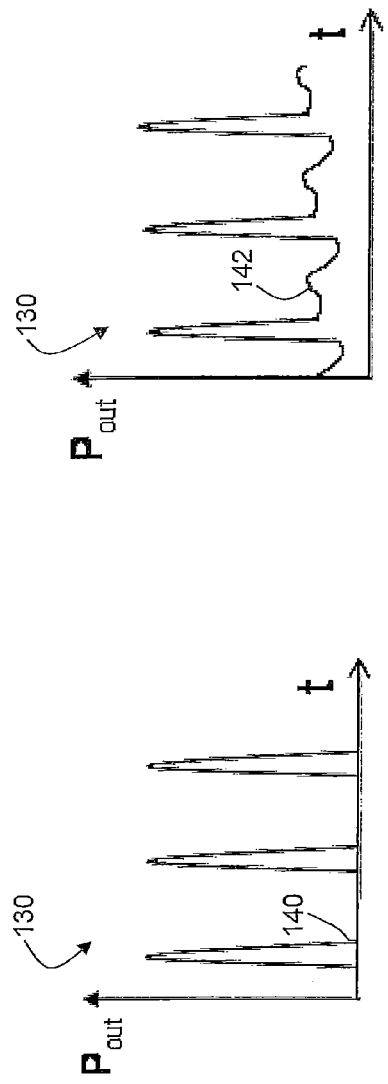
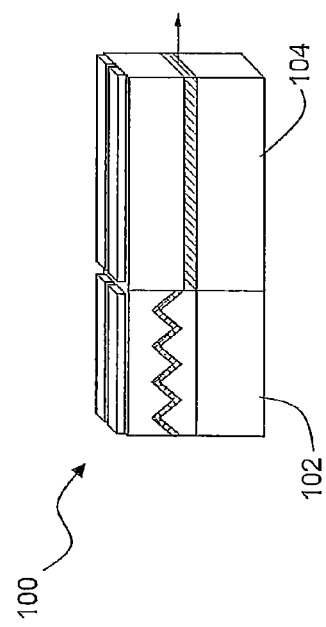
Fig. 3A
Fig. 3B
Fig. 4

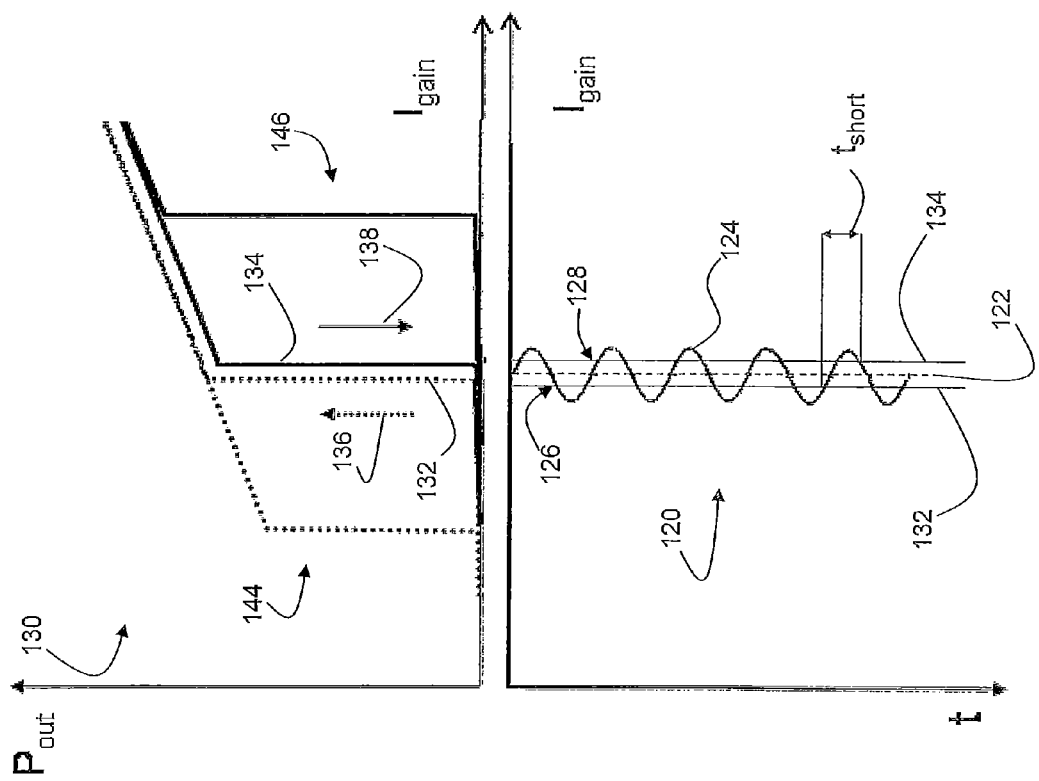

METHODS FOR OPERATING DIODE LASERS

BACKGROUND

The present disclosure relates to methods for operating lasers, and, more particularly, to methods for operating DBR diode lasers.

BRIEF SUMMARY

According to one embodiment, method for operating a diode laser is provided. According to the method, the diode laser comprises a wavelength selection section, a gain section and a saturable absorber. The method comprises applying a hybrid-control signal comprising a hybrid-control DC bias to the saturable absorber, and applying a hybrid-driving signal comprising a hybrid-driving DC bias and a hybrid-driving AC bias to the gain section. The hybrid signals are selected and the diode laser is configured such that a relatively high hybrid-control DC bias corresponds to a relatively low average of the output power of the diode laser, and a relatively low hybrid-control DC bias corresponds to a relatively high average of the output power of the diode laser. The hybrid-driving DC bias is between a switch-on threshold of the diode laser and a switch-off threshold of the diode laser, and the hybrid-driving AC bias is periodic. The hybrid-driving AC bias has a peak-to-peak amplitude greater than the difference between the switch-on threshold and the switch-off threshold.

Additional embodiments are disclosed and claimed.

BRIEF DESCRIPTION OF THE DRAWINGS

The following detailed description of specific embodiments of the present disclosure can be best understood when read in conjunction with the following drawings, where like structure is indicated with like reference numerals and in which:

FIG. 3A is a graphical depiction of the output power of a diode laser over time;

FIG. 3B is a graphical depiction of the output power of a diode laser over time;

FIG. 4 is a schematic depiction of a two section DBR diode laser;

FIG. 6 is a graphical depiction of the relationship between output power of a diode laser and the current applied to the gain section of a diode laser, and the current applied to the gain section over time.

DETAILED DESCRIPTION OF THE PREFERRED EMBODIMENTS

For the purposes of describing and defining the present disclosure it is noted that the term "hybrid" is used in a holistic manner and refers to the use of heterogeneous elements to form the composite methods of the present disclosure. Thus, when a signal is described as being hybrid, it indicates that the signal is an element of a method for operating a diode laser 10. Additionally, it is noted that, electrical quantities such as currents, voltages and the like are readily used interchangeably when describing the operation or control of electronic devices. Thus, while electrical quantities are described herein as currents, such descriptions are primarily for the purpose of clarity, and the present disclosure should not be so limited.

Figure 1:
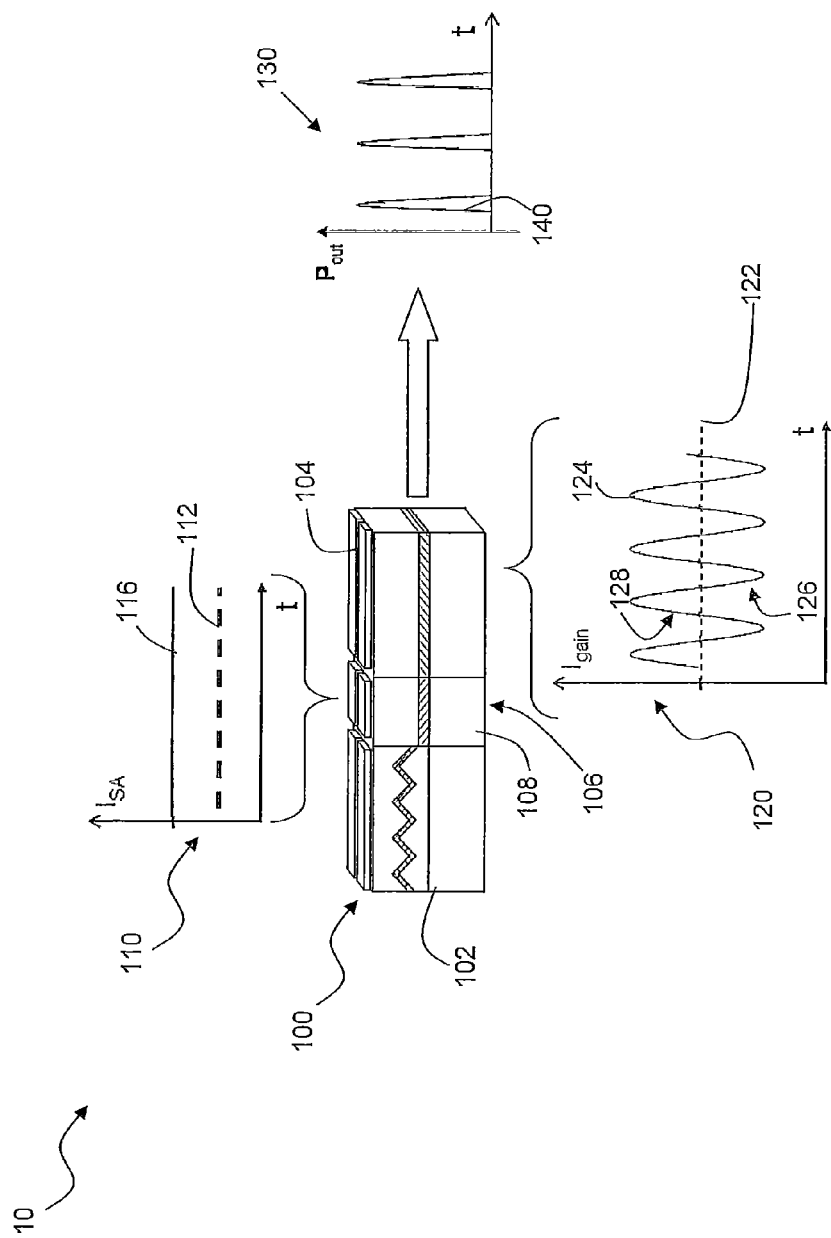
FIG. 1 is a schematic depiction of an embodiment of a method for operating DBR diode laser.

A method for operating a diode laser 10 according to one embodiment of the present disclosure is illustrated in FIG. 1. The diode laser 100, illustrated in FIG. 1, comprises a wavelength selection section 102, a gain section 104 and a saturable absorber 106. According to the method, a hybrid-control signal 110 and a hybrid-driving signal 120 are applied to the diode laser 100. The hybrid-control signal 110, which is depicted as a current applied to the saturable absorber 106 ($I_{SA}$), comprises a hybrid-control DC bias 112. Similarly, the hybrid-driving signal 120, comprising a hybrid-driving DC bias 122 and a hybrid-driving AC bias 124, is applied to the gain section 104. The hybrid signals 110 and 120 are selected and the diode laser 100 is configured such that a relatively high hybrid-control DC bias 112 corresponds to a relatively low average of the output power 130 of the diode laser 100. While, a relatively low hybrid-control DC bias 112 corresponds to a relatively high average of the output power 130 of the diode laser 100. The hybrid-driving signal 120 will be described in more detail below.

Figure 2:
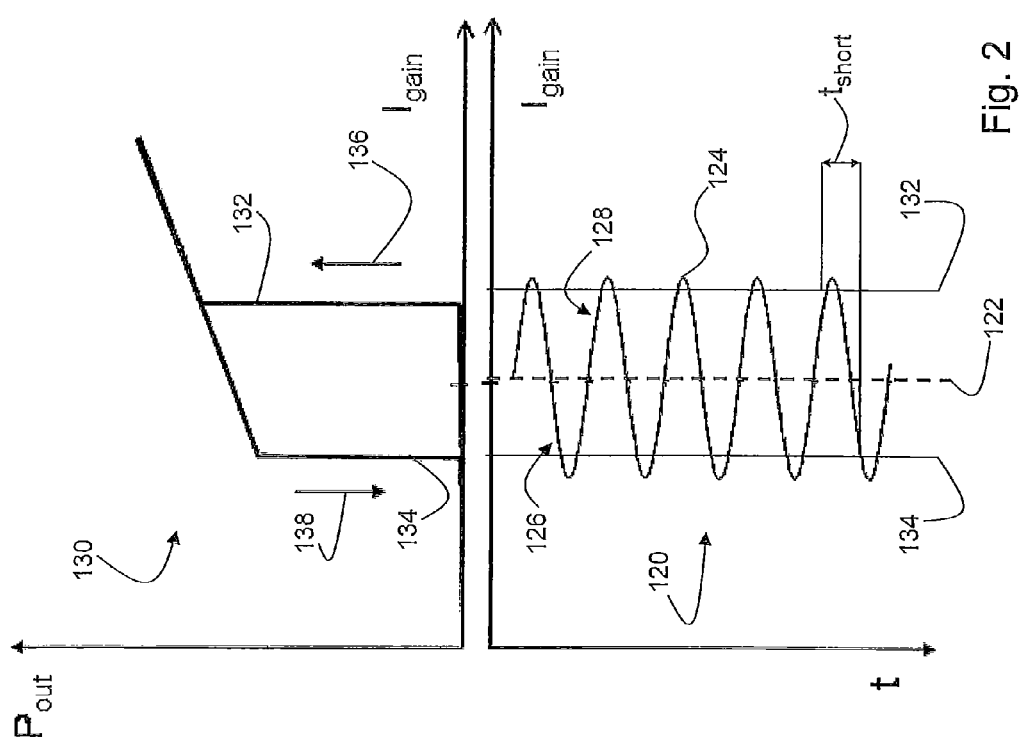
FIG. 2 is a graphical depiction of the relationship between output power of a diode laser and the current applied to the gain section of a diode laser, and the current applied to the gain section over time.

Referring now to FIG. 2, which depicts the output power 130 ($P_{out}$) as a function of current applied to the gain section ($I_{gain}$) and the current applied to the gain section ($I_{gain}$) over time (t), details of the hybrid-driving signal 120 can be observed. As described hereinabove, the hybrid-driving signal 120 comprises a hybrid-driving DC bias 122 and a hybrid-driving AC bias 124. The hybrid-driving DC bias 122 is between a switch-on threshold 132 of the diode laser 100 and a switch-off threshold 134 of the diode laser 100. Additionally, the hybrid-driving AC bias 124 is periodic with a peak-to-peak amplitude greater than the difference between the switch-on threshold 132 and the switch-off threshold 134. Thus, for example, when the hybrid-driving signal 120 is a current, the amperage varies over time between a maximum value greater than the switch-on threshold 132 and a minimum value below the switch-off threshold 134.

For the purpose of describing and defining the present disclosure, the term "switch-on threshold," as used herein, means the amount of electrical signal that needs to be applied to the gain section 104 of a diode laser 100 to transition the diode laser 100 from a superluminescent state to a lasing state. For example, as depicted in FIG. 2, as current applied to the gain section ($I_{gain}$) is increased beyond the switch-on threshold 132, the laser abruptly transitions from the superluminescent state to the lasing state with an abrupt output light power jump 136. The term "switch-off threshold," as used herein, means the amount of electrical signal that needs to be applied to the gain section 104 of a diode laser 100 to transition the diode laser 100 from a lasing state to a superluminescent state. Referring still to FIG. 2, as current applied to the gain section ($I_{gain}$) is decreased below the switch-off threshold 134, the laser abruptly switches from the lasing state to the superluminescent state with an abrupt output light power drop 138.

In an embodiment of the present disclosure, the hybrid-driving signal 120 reaches a value below the switch-off threshold 134 during a negative half period of the hybrid-driving signal 126. Also, the hybrid-driving signal 120 reaches a value above the switch-on threshold 132 during a positive half period of the hybrid-driving signal 128. In other embodiments of the method, the hybrid-driving signal 120 includes a hybrid-driving DC bias 122 within approximately +/−50% of an average of the switch-on threshold 132 and the switch-off threshold 134. In other embodiments, the hybrid-driving DC bias 122 is approximately equal to the average of the switch-on threshold 132 and the switch-off threshold 134. In further embodiments, the hybrid-driving AC bias 124 is sinusoidal. However, while some embodiments comprise a sinusoidal periodic signal, it should be understood the present disclosure contemplates the use of any type of periodic signal, such as, a square wave, a triangular wave, pulsed signal, irregular signal, and the like.

Referring now to FIGS. 3A and 3B, in an embodiment of a method for operating a diode laser 10, the hybrid-driving signal 120 is above the switch-on threshold 132 for a short duration of time ($t_{short}$) per period of the hybrid-driving signal 120 such that a shoulder-free output light pulse 140 is formed. As can be seen in FIG. 2, $t_{short}$ corresponds to a time period that is smaller than the period of the hybrid-driving signal 120. For example, $t_{short}$ may be in a of range of approximately 200 ps to approximately 50 ps when the hybrid-driving signal 120 has a frequency in a range of approximately 0.5 GHz to approximately 2.0 GHz. It should be noted that the previously described values of $t_{short}$ are primarily intended to demonstrate that $t_{short}$ is smaller than the period of the hybrid-driving signal 120, and thus, should not be read as a limitation of the present disclosure. Referring again to FIG. 3B, a shoulder 142 may be formed when the hybrid-driving signal 120 injects a total number of charge carriers (electrons and holes) into the diode laser 100 that exceeds the number charge carriers that are swept away during the first relaxation oscillation peak. For example, when $t_{short}$ or the amplitude of the hybrid-driving signal 120 are too large the diode laser 100 emits beyond the first relaxation oscillation peak, such as, the second relaxation oscillation peak, the third relaxation oscillation peak and so on.

With Reference to FIGS. 1 and 4, additional embodiments of the present disclosure are described. In one embodiment, the diode laser 100 (FIG. 4) is a DBR laser comprising two sections, such as, but not limited to, a wavelength selection section 102 and a gain section 104. The saturable absorber 106 (not shown in FIG. 4) may be a portion of either of, or both of, the wavelength selection section 102 and gain section 104. In another embodiment, the diode laser 100 (FIG. 1) is a three section DBR laser comprising a phase section 108 operating as a saturable absorber 106. In some embodiments, the saturable absorber 106 is disposed between the wavelength selection section 102 and the gain section 104. In other embodiments, the diode laser 100 is structured such that the gain section 104 is disposed between the wavelength selection section 102 and the saturable absorber 106.

Referring again to FIG. 1, in additional embodiments of a method for operating a diode laser 10, the hybrid-control DC bias 112 is below a saturable absorber threshold 116. For example, when a phase section 108 is active (with doping), the phase section 108 can operate as a saturable absorber 106 by applying a hybrid-control DC bias 112 that is below the saturable absorber threshold 116 (i.e., a current that is positive and below the saturable absorber threshold, zero or negative). Conversely, the phase section 108 can operate as an amplifier by applying a hybrid-control DC bias 112 that is positive and above the saturable absorber threshold 116.

Further embodiments of the present disclosure comprise varying the average of the output power 130 of the diode laser 100 by changing an amplitude of the hybrid-control DC bias 112. Some embodiments comprise changing the hybrid-driving signal 120, wherein a change in an amplitude of the hybrid-driving DC bias 122 is approximately proportional to a change in a peak-to-peak amplitude of the hybrid-driving AC bias 124. In embodiments such as, but not limited to, a laser source for a scanning laser projector, the hybrid-driving signal 120 is changed according to a look-up table or dynamically.

Figure 5:
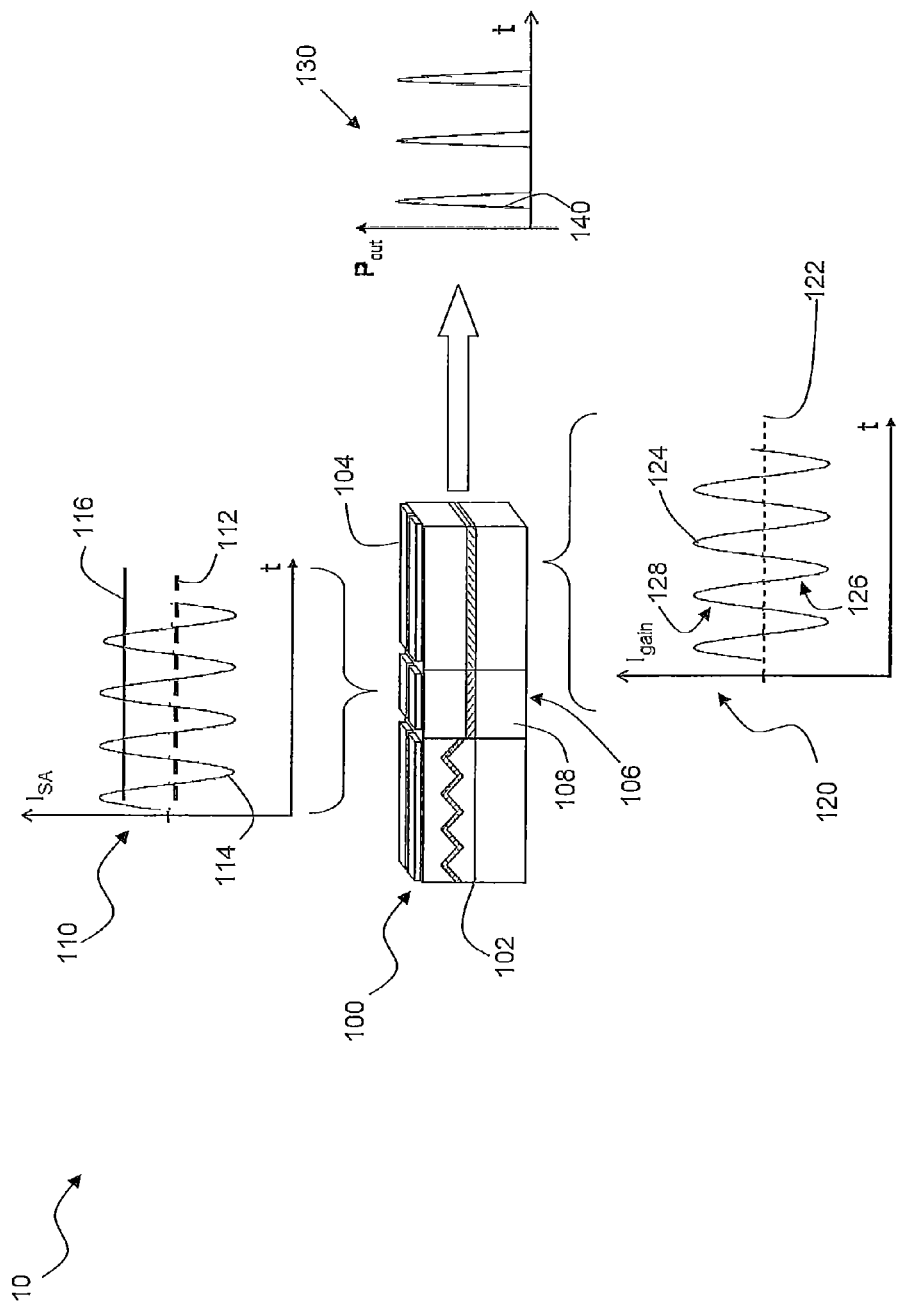
FIG. 5 is a schematic depiction of an embodiment of a method for operating DBR diode laser.

Referring now to FIGS. 5 and 6, it can be seen that in additional embodiments the hybrid-control signal 110 comprises a hybrid-control AC bias 114 that is periodic and has approximately the same frequency as the hybrid-driving AC bias 124. In further embodiments, the hybrid-control AC bias 114 corresponds with the hybrid-driving AC bias 124 such that a switch-on threshold 132 of the diode laser 100 is lower 144 during a positive half-period of the hybrid-driving signal 128 (depicted as the portion of the sinusoidal signal where $I_{gain}$ is increasing with respect to time) and a switch-off threshold 134 of the laser diode 100 is higher 146 during a negative half period of the hybrid-driving signal 126 (depicted as the portion of the sinusoidal signal where $I_{gain}$ is decreasing with respect to time). In some embodiments of the method, the hybrid-control AC bias 114 is in phase with the hybrid-driving AC bias 124. For example, the phase difference between the biases 114 and 124 is approximately $2n\pi$, where n is an integer.

In still further embodiments, as depicted in FIG. 6, the hybrid-control AC bias 114 (not shown) has a peak-to-peak amplitude such that the switch-on threshold 132 and the switch-off threshold 134 are within approximately +/−10% of one another. In additional embodiments of the method, the hybrid-control AC bias 114 has a peak-to-peak amplitude such that the switch-on threshold 132 and the switch-off threshold 134 are approximately equal.

Referring again to FIGS. 5 and 6, an embodiment comprises varying an average of the output power 130 wherein the hybrid-control AC bias 114 has a peak-to-peak amplitude such that the switch-on threshold 132 and the switch-off threshold 134 are within approximately +/−10% of one another. In additional embodiments, the peak-to-peak amplitude of the hybrid-driving AC bias 124 remains constant, and the hybrid-driving DC bias 122 is approximately equal to the switch-on threshold 132 or the switch-off threshold 134. In further embodiments, the peak-to-peak amplitude of the hybrid-driving AC bias 124 and the peak-to-peak amplitude of the hybrid-control AC bias 114 remain constant, while the hybrid-driving DC bias 122 and the hybrid-control DC bias 112 are changed to vary the average of the output power 130. In embodiments such as, but not limited to, a laser source for a scanning laser projector, the hybrid-driving DC bias and the hybrid-control DC bias are changed according to a look-up table or dynamically via, for example, using electronic feedback from a monitor photodiode.

For the purposes of describing and defining the present disclosure it is noted that "signal" refers to a quantity of electric charge, electromagnetic radiation, and the like. Additionally, the terms "apply," "applied," and other forms of the verb are utilized herein to refer to the transfer of electric charge, electromagnetic radiation, and the like. Thus, when a signal is applied to a section of a laser, electric charge, for example, is transferred to the section from the source of the signal.

It is noted that the term "approximately" is utilized herein to represent the inherent degree of uncertainty that may be attributed to any quantitative comparison, value, measurement, or other representation. The term "approximately" is also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A method for operating a diode laser, wherein the diode laser comprises a wavelength selection section, a gain section and a saturable absorber, the method comprising:
applying a hybrid-control signal comprising a hybrid-control DC bias to the saturable absorber; and
applying a hybrid-driving signal comprising a hybrid-driving DC bias and a hybrid-driving AC bias to the gain section, wherein the hybrid signals are selected and the diode laser is configured such that:
a relatively high hybrid-control DC bias corresponds to a relatively low average of the output power of the diode laser;
a relatively low hybrid-control DC bias corresponds to a relatively high average of the output power of the diode laser;
the hybrid-driving DC bias is between a switch-on threshold of the diode laser and a switch-off threshold of the diode laser;
the hybrid-driving AC bias is periodic; and
the hybrid-driving AC bias has a peak-to-peak amplitude greater than the difference between the switch-on threshold and the switch-off threshold.

2. The method of claim 1 wherein the hybrid-driving signal reaches a value below the switch-off threshold during a negative half period of the hybrid-driving signal and the hybrid-driving signal reaches a value above the switch-on threshold during a positive half period of the hybrid-driving signal.

3. The method of claim 2 wherein the hybrid-driving DC bias is within approximately +/−50% of an average of the switch-on threshold and the switch-off threshold.

4. The method of claim 2 wherein the hybrid-driving signal injects a total number of charge carriers into the diode laser such that a shoulder-free output light pulse is formed.

5. The method of claim 1 wherein the diode laser is a DBR laser comprising two sections.

6. The method of claim 1 wherein the diode laser is a three section DBR laser comprising a phase section operating as the saturable absorber.

7. The method of claim 1 wherein the hybrid-control DC bias is below a saturable absorber threshold.

8. The method of claim 1 further comprising varying an average of the output power of the diode laser by changing an amplitude of the hybrid-control DC bias.

9. The method of claim 8 further comprising changing the hybrid-driving signal, wherein a change in an amplitude of the hybrid-driving DC bias is approximately proportional to a change in a peak-to-peak amplitude of the hybrid-driving AC bias.

10. The method of claim 9 wherein the hybrid-driving signal is changed according to a look-up table or dynamically.

11. The method of claim 1 wherein:
the hybrid-control signal further comprises a hybrid-control AC bias; and
the hybrid-control AC bias is periodic and has approximately the same frequency as the hybrid-driving AC bias.

12. The method of claim 11 wherein the hybrid-control AC bias corresponds with the hybrid-driving AC bias such that a switch-on threshold of the diode laser is lower during a positive half-period of the hybrid-driving signal and a switch-off threshold of the laser diode is higher during a negative half period of the hybrid-driving signal.

13. The method of claim 12 wherein the hybrid-control AC bias is in phase with the hybrid-driving AC bias.

14. The method of claim 11 wherein the hybrid-control AC bias has a peak-to-peak amplitude such that the switch-on threshold and the switch-off threshold are within approximately +/−10% of one another.

15. The method of claim 14 wherein the hybrid-control AC bias has a peak-to-peak amplitude such that the switch-on threshold and the switch-off threshold are approximately equal.

16. The method of claim 11 further comprising varying an average output power wherein the hybrid-control AC bias has a peak-to-peak amplitude such that the switch-on threshold and the switch-off threshold are within approximately +/−10% of one another.

17. The method of claim 16 wherein:
a peak-to-peak amplitude of the hybrid-driving AC bias remains constant; and
the hybrid-driving DC bias is nearly equal to the switch-on threshold or the switch-off threshold.

18. The method of claim 16 wherein:
a peak-to-peak amplitude of the hybrid-driving AC bias and the peak-to-peak amplitude of the hybrid-control AC bias remain constant; and
the hybrid-driving DC bias and the hybrid-control DC bias are changed.

19. The method of claim 18 wherein the hybrid-driving DC bias and the hybrid-control DC bias are changed according to a look-up table or dynamically.

20. A method for operating a diode laser, wherein the diode laser comprises a wavelength selection section, a gain section and a phase section operating as a saturable absorber, the method comprising:
applying a hybrid-control signal comprising a hybrid-control DC bias or a hybrid-control DC bias and a hybrid-control AC bias to the saturable absorber; and
applying a hybrid-driving signal comprising a hybrid-driving DC bias and a hybrid-driving AC bias to the gain section, wherein the hybrid signals are selected and the diode laser is configured such that:
a relatively high hybrid-control DC bias corresponds to a relatively low average of the output power of the diode laser;
a relatively low hybrid-control DC bias corresponds to a relatively high average of the output power of the diode laser;
the hybrid-control DC bias is below a saturable absorber threshold;
the hybrid-driving DC bias is between a switch-on threshold of the diode laser and a switch-off threshold of the diode laser;
the hybrid-driving AC bias is periodic;
the hybrid-driving AC bias has a peak-to-peak amplitude greater than the difference between the switch-on threshold and the switch-off threshold;
the hybrid-driving signal reaches a value below the switch-off threshold during a negative half period of the hybrid-driving signal; and
the hybrid-driving signal reaches a value above the switch-on threshold during a positive half period of the hybrid-driving signal.

* * * * *